United States Patent [19]

Bruner, Jr.

[11] Patent Number: 5,166,421
[45] Date of Patent: Nov. 24, 1992

[54] PROCESS FOR THE MANUFACTURE OF ADIPIC ACID

[75] Inventor: Harold S. Bruner, Jr., Hockessin, Del.

[73] Assignee: E. I. du Pont De Nemours and Company, Wilmington, Del.

[21] Appl. No.: 671,155

[22] Filed: Mar. 18, 1991

[51] Int. Cl.$^5$ ................ C07C 51/10; C07C 51/353
[52] U.S. Cl. ................................ 562/522; 562/591
[58] Field of Search .......................... 562/522, 591

[56] References Cited

U.S. PATENT DOCUMENTS

| | | | |
|---|---|---|---|
| 4,622,423 | 11/1986 | Burke | 562/522 |
| 4,788,333 | 11/1988 | Burke | 562/522 |
| 4,939,298 | 7/1990 | Burke | 562/591 |

*Primary Examiner*—Arthur C. Prescott
*Attorney, Agent, or Firm*—Earl L. Handley

[57] ABSTRACT

A process for the manufacture of adipic acid by reacting 1,3-butadiene or an allylic butenol or the like with carbon monoxide and water using a rhodium catalyst and an HI or HBr promoter, removing adipic acid from the reaction mixture, and reacting at least part of the remaining portion of the reaction mixture to form additional adipic acid.

6 Claims, No Drawings

PROCESS FOR THE MANUFACTURE OF ADIPIC ACID

FIELD OF THE INVENTION

This invention relates to a process for the manufacture of adipic acid.

BACKGROUND OF THE INVENTION

The dominant commercial process for the manufacture of adipic acid involves the air-oxidation of cyclohexane to form a mixture of cyclohexanol and cyclohexanone, which is subsequently oxidized by nitric acid to form a mixture of carboxylic acids, including adipic acid. Disadvantages of this process include low initial conversion of cyclohexane, formation of nitrated by-products, and generation of large wastewater and wastegas streams. Consequently, efforts have been made to find alternate routes to adipic acid.

Von Kutepow has disclosed the production of adipic acid by the reaction of butadiene, carbon monoxide and water at elevated temperature and pressure and in the presence of a halogen-promoted rhodium catalyst and an aromatic or saturated aliphatic solvent (U.S. Pat. No. 3,876,695). Yields of adipic acid range from 23% to about 50%.

Burke has disclosed a two-step route to adipic acid which comprises hydrocarboxylating butadiene to unsaturated $C_5$ monocarboxylic acids in selected halocarbon solvents using an iodide-promoted rhodium catalyst, and then further hydrocarboxylating these $C_5$ acids to adipic acid using the same catalyst system and solvent. The preferred temperature for the first step is 100°-60° C., while that of the second step is 150°-180° C. (U.S. Pat. No. 4,622,423 and U.S. Pat. No. 4,788,333). Although the linear selectivity of these reactions is high, and the over-all yield of adipic acid is substantially over 50%, the rates of reaction, especially that of the first step, are relatively low.

Burke has disclosed that the rhodium-catalyzed, iodide-promoted, hydrocarboxylation of certain unsaturated esters and terminally unsaturated alkenes can be accelerated by the addition of aliphatic or aromatic acids, having a pKa in the range of 4.2 to 5.2 (U.S. Pat. No. 4,788,334). However, the use of such accelerators results in a decrease in the linearity of the hydrocarboxylated products.

Burke has disclosed the interconversion of linear and branched saturated alkyl carboxylic acids by heating in the presence of an iodide or bromide promoted rhodium catalyst and carbon monoxide (U.S. Pat. No. 4,939,298).

The process of this invention seeks to overcome the disadvantages of the prior art by providing a high yield, high-rate, low-pollution process for the manufacture of adipic acid.

SUMMARY OF THE INVENTION

This invention provides a process for the manufacture of adipic acid which comprises the steps of: (a) reacting a hydrocarboxylatable compound chosen from the group consisting of 1,3-butadiene, allylic butenols, ethers of allylic butenols, and esters of allylic butenols, with carbon monoxide and water in the presence of a rhodium catalyst and a halide promoter chosen from the group consisting of HI and HBr, at a temperature of about 50° C. to about 250° C. and at a carbon monoxide partial pressure of from about 100 psi to about 3,000 psi, wherein the molar ratio of promoter to rhodium is between about 1:1 and about 20:1, and the concentration of water is maintained below about 20 weight %, to form a reaction mixture containing adipic acid and branched $C_6$ dicarboxylic acids;

(b) recovering adipic acid from the reaction mixture produced in step (a); and (c) heating at least part of the remaining portion of the reaction mixture at a temperature of about 170° C. to about 250° C. in the presence of carbon monoxide, water, a rhodium catalyst, and a halide promoter chosen from the group consisting of HI and HBr, wherein the carbon monoxide partial pressure is from about 200 psi to about 10,000 psi, the molar ratio of promoter to rhodium is between about 1:1 and about 20:1, and the concentration of water is less than about 50 weight %, to isomerize branched $C_6$ dicarboxylic acids contained therein to adipic acid.

DETAILED DESCRIPTION OF THE INVENTION

This invention provides an efficient, potentially low pollution route to adipic acid, based on the HI- or HBr-promoted, rhodium-catalyzed hydrocarboxylation of 1,3-butadiene or butadiene derivatives, such as allylic butenols, and esters or ethers of allylic butenols. Critical features of this invention include the use of relatively low molar ratios of promoter-to-Rh during steps (a) and (c) to maintain high selectivity to linear products and low production of saturated by-products, and the isolation of a substantial portion of the desired adipic acid before step (c), in which a mixture of $C_6$ dicarboxylic acids is heated in the presence of water, carbon monoxide and the halogen-promoted rhodium catalyst to produce additional adipic acid.

Suitable hydrocarboxylatable compounds for step (a) include: 1,3-butadiene; the allylic butenols, 3-buten-2-ol and 2-buten-1-ol; ester derivatives of the allylic butenols, R'COOR, wherein R is

and R' is $C_1$–$C_{10}$ alkyl or $C_6$–$C_{10}$ aryl; and, ether derivatives, R—O—R', wherein R and R' are as defined above. These materials are commercially available, or can be made by standard routes.

In a preferred embodiment of this invention, step (a) is carried out in two stages, differentiated by temperature and determined by the extent of conversion of the hydrocarboxylatable compound. The optimum temperature for the first stage of step (a) depends on the choice of hydroxylatable substrate. When butadiene is used as the hydrocarboxylatable compound, the preferred temperature range for the first stage of step (a) is from 100° C. to 180° C., more preferably 130° C. to 160° C. When the allylic alcohols, allylic butenol esters or ethers are used as the hydrocarboxylatable compound, the preferred temperature in the first stage is from 50° C. to 150° C., more preferably 100° C. to 135° C.

In the preferred embodiment of this invention, the hydrocarboxylatable compound (butadiene, allylic butenol, allylic butenol ester or ether) is reacted in the first stage of step (a) with CO (and, in the case of butadiene, water) to form predominantly 3-pentenoic acid and minor amounts of other unsaturated $C_5$ monocarboxylic acids and lactones. When substantially all (90–99.9%) of the hydrocarboxylatable compound has reacted, the temperature is increased to 180° C. to 250° C., preferably 190° C. to 230° C., wherein the 3-pentenoic and other unsaturated $C_5$ monocarboxylic acids produced in the first stage are further reacted with CO and water in a second stage to form a mixture of adipic acid and other $C_6$ dicarboxylic acids.

Step (b), the recovery of the desired adipic acid, can be accomplished in one of several ways. For example, the reaction mixture produced in step (a) can be cooled to induce the crystallization of adipic acid, and the crystalline product isolated by filtration. Alternatively, a solvent such as toluene can be added to the reaction mixture from step (a) to cause the preferential crystallization of adipic acid. Other methods of selectively removing adipic acid from the reaction mixture of step (a) can also be used. Suitable temperatures for step (b) will be largely determined by the method used to isolate the adipic acid, but should not exceed about 210° C. Temperatures of 10° C. to 100° C. are preferred. For high yields of adipic acid from the process of this invention, it is important to remove selectively as much adipic acid as possible from the reaction mixture in step (b), because some of the adipic acid which remains in the second fraction will isomerize to branched $C_6$ dicarboxylic acids under the reaction conditions of step (c).

The preferred temperature in step (c) is about 180° C. to 250° C., more preferably 190° C. to 250° C., and most preferably 200° C. to 240° C.

An important feature of this process is that it uses the same catalyst system (HI- or HBr-promoted rhodium catalyst) for all three chemical reactions occurring in steps (a) and (c): 1. hydrocarboxylation of butadiene or the allylic butenol compounds to unsaturated $C_5$ monocarboxylic acids; 2. further hydrocarboxylation of the unsaturated $C_5$ monocarboxylic acids to adipic acid (and other $C_6$ dicarboxylic acids); and 3. isomerization of $C_6$ dicarboxylic acids, such as 2-methylglutaric, dimethylsuccinic and ethylsuccinic acids, to adipic acid. This process can be carried out in a batch or continuous mode. In either type of operation, but especially in a continuous mode, it is advantageous to use the product mixture from step (c) as the solvent for step (a). In this way, the adipic acid made in step (c) is recycled through step (a) to be isolated in step (b), and the expensive rhodium catalyst is also recycled through the process.

It is not necessary that all of the portion of the reaction mixture remaining after recovery of adipic acid per step (b), be subjected to isomerization per step (c). For example a portion of the reaction mixture product from step (b) can, in a continuous process, be recycled directly to step (a) where it serves as solvent for step (a), and a portion of the reaction mixture product from step (b) can be subjected to isomerization conditions per step (c) and this portion then recycled to step (a) where it also serves as solvent for step (a), and the adipic acid formed in the isomerization can be removed when the mixture passes to step (b). Likewise a portion of the reaction mixture product from step (b) can be subjected to isomerization per step (c) and all or a portion of the product from step (c) by cycled to step (b) to recover the adipic acid formed by isomerization in step (c). Of course the adipic acid formed in step (c) can be recovered directly from this step (c) mixture. Other alternatives and variations are within the scope of the present invention. It is however, preferred when operating in a continuous manner to cycle the entire product mixture after removal of adipic acid per step (b), to step (c) and to recycle the entire product of step (c) to step (a).

Another important feature of this process is that the over-all yield of adipic acid is significantly increased by the isomerization of branched $C_6$ dicarboxylic acids such as 2-methylglutaric, ethylsuccinic and 2,3- dimethylsuccinic acid, to adipic acid in step (c). This conversion of less desirable branched by-products into linear acid also obviates a separate purge point for the branched products in a continuous process.

When the hydrocarboxylatable compound used in step (a) is 1,3-butadiene, a solvent must be used in this step to keep the concentration of butadiene low enough to avoid the formation of large amounts of butadiene oligomers. Preferably, the solvent is about 65% to about 98% and butadiene is below about 20% by weight of the reaction mixture. When other hydrocarboxylatable compounds are used, the use of a solvent is preferred, but not necessary. Suitable solvents for step (a) are aliphatic $C_2$-$C_{20}$ monocarboxylic acids, aliphatic $C_4$-$C_{20}$ dicarboxylic acids, benzoic acid, alkyl-substituted benzoic acids, $C_6$-$C_{10}$ aromatic solvents and mixtures thereof. Preferred solvents are aliphatic $C_2$-$C_6$ monocarboxylic acids, $C_4$-$C_7$ dicarboxylic acids, benzoic acid, $C_6$-$C_8$ aromatic solvents, and mixtures thereof. More preferred solvents are benzene, toluene, acetic acid, propionic acid, butyric acid, 2-methylbutyric acid, 2-methylpropionic acid, valeric acid, caproic acid, and mixtures thereof. Mixtures of monocarboxylic and dicarboxylic acids produced in this process can also be used in whole or in part as the solvent for this process. Such monocarboxylic and dicarboxylic acids include, but are not limited to, adipic, valeric, 2-methyl-glutaric, ethylsuccinic, dimethylsuccinic and methylbutyric acids. In a continuous operation, the most preferred solvent for step (a) is the reaction mixture from step (c).

If the adipic acid-depleted portion isolated from step (b) is a liquid under the reaction conditions of step (c), no additional solvent is necessary for step (c). However, it may be desirable to add additional solvents, in which case suitable solvents are the carboxylic acid and aromatic solvents described above.

Water is necessary for the complete hydrocarboxylation of butadiene and the allylic butenol compounds in step (a). Water is also necessary to maintain catalyst stability during the isomerization of the $C_6$ dicarboxylic acids in step (c). The water required for these operations can be obtained from water added to the reaction mixture or from water formed under the reaction conditions (for example, from the formation of esters or anhydrides). However, water should not be present in large excess during steps (a) and (c). When the hydroxylatable compound used in step (a) is butadiene, water is preferably present in an amount of less than 15%, more preferably less than 10%, and most preferably less than 5%, based on the weight of the reaction mixture. (The weight of the reaction mixture includes the weight of the solvent(s), catalyst(s), promoter(s), and reactants). When an allylic butenol, or an allylic butenol ester, is present in the reaction mixture, the amount of water present is preferably less than 5% by weight. The water can be present in the solution at the beginning of the reaction, or it can be added continuously as it is consumed to avoid undesirably high concentrations.

The rhodium catalyst can be provided from any source or by any material which will produce rhodium ions under hydrocarboxylation conditions. Among the materials which can be employed as the source of the rhodium catalyst are rhodium metal, rhodium salts, rhodium oxides, rhodium carbonyl compounds, organorhodium compounds, coordination compounds of rhodium and mixtures thereof. Specific examples of such materials include, but are not limited to, rhodium-(III) chloride and its hydrates, $RhI_3$, $Rh(CO)_2I_3$, $Rh(CO)I_3$, rhodium(III) nitrate trihydrate, $Rh_4(CO)_{12}$, $Rh_6(CO)_{16}$, $Rh(acac)_3$, $Rh(CO)_2(acac)$, $Rh(C_2H_4)_2(acac)$, $[Rh(C_2H_4)_2Cl]_2$, $[Rh(CO)_2Cl]_2$, $Rh(COD)(acac)$, $[Rh(COD)Cl]_2$, $[Rh(CO_2I]_2$, $RhCl(CO)$ $(PPH_3)_2$, $Rh_2[O_2C(CH_2)_6CH_3]_4$ and $Rh_2(acetate)_4$, where acac is acetylacetonate and COD is 1,5-cyclooctadiene. Supported rhodium compounds, e.g., Rh/C and Rh/alumina, can also be used as a source of the rhodium catalyst. Rhodium compounds containing bidentate phosphine or nitrogen ligands should be avoided. Preferred sources of the rhodium catalyst include rhodium(I) compounds such as $[Rh(CO)_2Cl]_2$, $[Rh(COD)Cl]_2$, $[Rh(CO)_2I]_2$ and $Rh(COD)(acac)$ and rhodium iodide compounds such as $RhI_3$ and $Rh(CO)_2I_3$.

Suitable concentrations of rhodium in steps (a) and (c) are in the range of 0.005–0.50% by weight of rhodium metal based on the weight of the reaction mixture. Preferably, the concentration of rhodium is in the range of 0.01–0.20 wt %, more preferably 0.02–0.10 wt %.

The rhodium catalyst, which can be preformed or formed in situ, must be promoted by HI or HBr, preferably HI, to achieve satisfactory reaction rates in steps (a) and (c). The promoter can be provided by HX (X=I, Br), $X_2$, MX (M=alkali metals), $M'X_2$ (M'=alkaline earth metals), transition metal bromides or iodides, organic iodides or bromides, or any other source which will provide HI or HBr under hydrocarboxylation conditions. Preferred sources of HI and HBr include HI, HBr, acetyl bromide, acetyl iodide, acetoxyiodobutane, aryl iodides, aryl bromides, lower alkyl bromides ($C_1$–$C_{10}$) and lower alkyl iodides $C_1$–$C_{10}$), such as methyl bromide, bromoethane, 1-bromopropane, 1-bromobutane, 1,4-dibromobutane, 2-bromoproprane, bromoheptane, methyl iodide, 2-iodobutane, iodoethane, 1-iodobutane, 1,4-diodobutane, 2-iodopropane, 1-iodopropane, and iodoheptane. The halide and rhodium can be present in the same compound, e.g., as in RhI'. The most preferred sources of promoters are HI, HBr, methyl iodide, and iodobutanes.

The molar ratio of promoter-to-rhodium in steps (a) and (c) should be between about 1 and about 20, preferably between about 2 and about 15.

EXAMPLE 1

Butadiene to Adipic Acid

STEP (a): Hydrocarboxylation of Butadiene. Adipic acid (8.7 g) and 2-methylglutaric acid (25.6 g) were dissolved in a mixture of water (4.5 g) and acetic acid (45.4 g). A 100 cc autoclave was charged with a 75 g portion of the acid mixture, pressured to 200 psi with $CO/H_2$ (99/1), and heated to 150° C. Upon reaching 150° C., the pressure was increased to 500 psi using the same gas mixture. The gas introduction was used to simultaneously inject aq. HI (57%, 0.4 g) and 1.78 g of an acetic acid/water solution (70/30) containing 2.89% rhodium and 7.85% iodide (as the $[Rh(CO)_2I_2]$-complex and free HI), followed by acetic acid (3 g). A pump was used over the next 2.4 min to inject 7.0 g of 1,3-butadiene. The pressure was increased to 600 psi with the same $CO/H_2$ gas mixture and was supplied on demand throughout the reaction to maintain 600 psi. Samples were removed after reaching 600 psi and again at 2, 4, 15, 30, 45, and 60 min after reaching 600 psi. (See Table 1 for analyses at 0 and 60 min.). The temperature was then increased to 200° C. and the pressure was increased to 700 psi. A sample was removed at 60 min after reaching the new temperature. The reaction was held at 200° C. for a total of 120 min.

TABLE 1

| Hydrocarboxylation of Butadiene | | |
|---|---|---|
| | Time | |
| | 0 min | 60 min |
| Butadiene | 5.03 | 0.57 |
| 2-Methylglutaric acid | 24.10 | 25.82 |
| Adipic Acid | 8.28 | 8.56 |
| trans-3-Pentenoic acid | 0.76 | 3.45 |
| cis-3-Pentenoic acid | 0.38 | 1.45 |
| Dimethylsuccinic acid | 0.00 | 0.00 |
| Ethylsuccinic acid | 0.00 | 0.02 |
| γ-Valerolactone | 0.00 | 0.00 |

Step (b): Crystallization of Adipic Acid. After 120 min at 200° C., the autoclave was cooled to 60° C. and the reaction mixture drained into a glass bottle fitted with a rubber septum cap and maintained under 10 psi of CO. Extensive adipic acid crystallization was immediately observed. A sample of the supernatant was taken for analysis.

| | Analysis (supernatant): |
|---|---|
| Butadiene | 0.06% |
| 2-Methylglutaric acid | 24.25 |
| Adipic acid | 7.55 |
| trans-3-Pentenoic acid | 0.01 |
| cis-3-Pentenoic acid | 0.29 |
| Dimethylsuccinic acid | 0.04 |
| Ethylsuccinic acid | 0.34 |
| γ-Valerolactone | 2.16 |
| Valeric acid | 0.79 |

More crystals formed while the reaction mixture was held for an additional 12 h at room temperature under 10 psi of CO. The resulting heterogeneous mixture was separated into two fractions: an upper, substantially homogeneous, adipic acid-depleted fraction (30.1 g), and a lower, heterogeneous fraction (16.1 g) which contained crystalline adipic acid.

Step (c): Isomerization of Dicarboxylic Acids.

The adipic acid-depleted sample from step (b) was returned to the autoclave and heated at 230° C. and 900 psi (using $CO/H_2$, 99/1) for 2 h, cooled to 60° C., and again drained into a glass bottle under a CO atmosphere. The autoclave was then rinsed with acetic acid (50 mL).

Analyses (in weight %) of the adipic acid-depleted fraction, adipic acid-enriched fraction, isomerization product (23.2 g), and autoclave rinse sample (50.5 g) are summarized in Table 2.

| | Adipic Acid Enriched | Adipic Acid Depleted | Isomerization Product | Rinse Sample |
|---|---|---|---|---|
| Adipic Acid | 19.28 | 4.04 | 5.71 | 0.25 |
| 2-Methylglutaric acid | 22.48 | 26.52 | 21.65 | 1.03 |
| trans-3-Pentenoic acid | 0.62 | 0.74 | 0.07 | 0.00 |
| cis-3-Pentenoic acid | 0.17 | 0.19 | 0.15 | 0.00 |
| Dimethylsuccinic acid | 0.02 | 0.02 | 0.18 | 0.00 |
| Ethylsuccinic acid | 0.31 | 0.37 | 0.66 | 0.03 |

-continued

| | Adipic Acid Enriched | Adipic Acid Depleted | Isomerization Product | Rinse Sample |
|---|---|---|---|---|
| γ-Valerolactone | 1.87 | 2.33 | 1.62 | 0.09 |
| Valeric acid | 0.72 | 0.84 | 2.16 | 0.00 |

EXAMPLE 2

Crotyl Alcohol to Adipic Acid

The crotyl alcohol used in this example was a commercial sample from Aldrich Chemical Company, and was predominantly a mixture of isomers of 2-butene-1-ol. The final product and all samples from the autoclave were analyzed by GC, directly for both monobasic acids and unreacted crotyl alcohol on a DB-FFAP capillary column, and as the methyl esters for dibasic acids on a CP-52 Carbowax capillary column. Internal standard (orthodichlorobenzene) was added to each sample to permit quantification of the components. Amounts are given as concentrations (g/500 mL). No other products were detected in significant amounts and no tars were formed.

Step (a)—First Stage: Crotyl Alcohol to Pentenoic Acid.

A 300 mL Hastelloy-C mechanically stirred autoclave was flushed with nitrogen and then with high purity carbon monoxide. It was then charged with a solution of [RH(CO)$_2$I]$_2$ (0.57 g, 1 mmol), aq. HI (57%, 2.35 g, 10.5 meq) and water (2.1 g, 117 mmol) in acetic acid (125 mL). The autoclave was closed, pressured with CO to 300 psi, heated to 125° C., and then crotyl alcohol (20.3 g, 282 mmol) was injected with CO pressure from a charge cylinder. The total pressure in the autoclave was 486 psi at 124° C. The pressure was maintained in the range 486–504 psi by feeding CO via a regulator valve from a reservoir at an initial pressure of 4095 psi. Crotyl alcohol carbonylation rate was measured by monitoring the reservoir pressure drop and by sampling liquid from the reactor. GC analysis of the reactor liquid showed that 100% of the crotyl alcohol had reacted after 25 min and that the major product was 3-pentenoic acid.

| Products of Step (a) - First Stage | |
|---|---|
| 2-Methylbutyric acid | 0.086 |
| Valeric acid | 0.150 |
| trans-4-Pentenoic acid | 0.051 |
| trans-3-Pentenoic acid | 9.507 |
| cis-3-Pentenoic acid | 3.405 |
| γ-Valerolactone | 0.319 |
| Ethylsuccinic acid | 0.165 |
| 2-Methylglutaric acid | 0.725 |
| Adipic acid | 0.218 |

Step (a)—Second Stage: Pentenoic Acids to Adipic Acid and Isomers.

When all of the crotyl alcohol had been converted (25 min) the reaction temperature was increased to 200° C. over 20 min to convert the pentenoic acid to adipic acid and branched C$_6$ dicarboxylic acids. Additional water (5.1 g, 282 mmole) was simultaneously added via a syringe pump. The temperature was held at 200° C. for 3 h, at which point GC analysis of the reactor liquid showed that most of the pentenoic acid and lactones had been converted to dibasic acids. The reaction mixture was then cooled to 80° C.

| Products of Step (a) - Second Stage | |
|---|---|
| 2-Methylbutyric acid | 0.703 |
| Valeric acid | 1.360 |
| trans-3-Pentenoic acid | 0.115 |
| cis-3-Pentenoic acid | 0.057 |
| γ-Valerolactone | 0.583 |
| Ethylsuccinic acid | 1.513 |
| 2-Methylglutaric acid | 6.756 |
| Adipic acid | 5.713 |

Step (b): Separation of Crude Adipic Acid.

The product from the reactor was discharged into a vented serum-capped bottle (which had previously been purged with CO) under CO pressure. On cooling to 0° C. most of the reaction product crystallized from solution. The reaction mixture was then allowed to sit at room temperature overnight, resulting in a large portion of the solid re-dissolving. The reaction mixture was then chilled in wet ice for about 30 min and transferred to a nitrogen-filled dry box, where most of the mother liquor was decanted from the crude adipic acid crystals into a charge cylinder for return to the reactor.

Outside the drybox, the crude crystalline sample with its retained mother liquor was chilled briefly again before filtering off the solid adipic acid. A portion of the retained mother liquor was taken for GC analysis. After filtering, the crude crystals were washed briefly with chilled toluene, then dried under vacuum; 6.2 g crude crystals were obtained. A portion of the crystals was dissolved in acetic acid and analyzed for adipic acid and other C$_6$ dibasic acids by GC as the methyl esters. The analysis showed adipic acid with just a trace of 2-methylglutaric acid.

Analysis of the retained mother liquor showed that it had been significantly and selectively depleted of adipic acid:

| Products of Step (b) - Retained Mother Liquor | |
|---|---|
| 2-Methylbutyric acid | 0.714 |
| Valeric acid | 1.384 |
| trans-3-Pentenoic acid | 0.054 |
| cis-3-Pentenoic acid | 0.032 |
| γ-Valerolactone | 0.59 |
| Ethylsuccinic acid | 1.851 |
| 2-Methylglutaric acid | 8.314 |
| Adipic acid | 2.886 |

Step (c): Isomerizaton of branched C$_6$ Dicarboxylic Acids to Adipic Acid.

The mother liquor (110 g) was returned to the reactor which had been flushed with CO. The reactor was then pressured with CO to 500 psi and the temperature was raised to 230° C.; the total pressure in the autoclave was 894 psi at 230° C. The reactor was maintained at 230° C. for a total of 5 h, with addition of 1.0 g water at 200 min of reaction, and then cooled to room temperature. The excess CO was vented through a control valve and the product was discharged. GC analysis of the liquid samples showed that the amount of adipic acid increased during isomerization.

| Isomerization Products | t = 0 min | t = 300 min |
|---|---|---|
| 2-Methylbutyric acid | 0.745 | 1.318 |
| Valeric acid | 1.442 | 1.751 |
| trans-3-Pentenoic acid | 0.088 | — |
| cis-3-Pentenoic acid | 0.045 | — |
| γ-Valerolactone | 0.604 | 0.623 |

-continued

| Isomerization Products | t = 0 min | t = 300 min |
|---|---|---|
| Ethylsuccinic acid | 1.898 | 2.358 |
| 2-Methylglutaric acid | 8.485 | 7.819 |
| Adipic acid | 3.481 | 4.663 |

I claim:

1. A process for the manufacture of adipic acid which comprises:
   (a) reacting in a solvent selected from the class consisting of aliphatic monocarboxylic acids having 2 to 20 carbon atoms, aliphatic dicarboxylic acids having 4 to 20 carbon atoms, benzoic acid, alkyl-substituted benzoic acids, aromatic solvents having 6 to 10 carbon atoms, and mixtures of these solvents, a compound selected from the class consisting of 1,3-butadiene, allylic butenols, esters of allylic butenols, and esters of allylic butenols with carbon monoxide and water in the presence of a rhodium catalyst and a halide promoter selected from the class consisting of HI and HBr, at a temperature of about 50 degrees C. to about 250 degrees C. and at a carbon monoxide partial pressure of from about 100 psi to about 3,000 psi, wherein the molar ratio of promoter to rhodium is between about 1:1 and about 20:1 and the concentration of water is maintained below about 20 weight %, to form a reaction mixture containing adipic acid and branched six carbon dicarboxylic acids;
   (b) recovering adipic acid form the reaction mixture produced in step (a); and
   (c) heating at least part of the remaining portion of the reaction mixture at a temperature of about 170 degrees C. to about 250 degrees C., and in the presence of carbon monoxide, water, a rhodium catalyst and a halide promoter selected from the class consisting of HI and HBr, wherein the carbon monoxide partial pressure is from about 200 psi to about 10,000 psi, the molar ratio of promoter to rhodium is between about 1:1 to about 20:1, and the concentration of water is less than about 50 weight %, to isomerize branched six carbon dicarboxylic acids contained therein to adipic acid.

2. The process of claim 1 in which step (a) is carried out in stages where in the first stage the compound is reacted at about 100° C. to 180° C. to form predominantly 3-pentenoic acid, and then the temperature is adjusted to be in the range of 180° C. to 250° C. and 3-pentenoic acid is reacted to form a reaction product containing adipic acid and branched six carbon dicarboxylic acids.

3. The process of claim 2 in which the compound is 1,3-butadiene and concentrate of 1,3-butadiene in the reaction mixture is below about 20% by weight.

4. The process of claim 1 which is carried out continuously and in which the product mixture of step (c) is cycled to step (a).

5. The process of claim 1 in which the compound reacted is an allylic butenol and the reaction temperature in step (a) is in the range of about 75 degrees C. to about 150 degrees C.

6. The process of claim 1 in which the adipic acid is recovered in step (b) by crystallization.

* * * * *